United States Patent [19]

Ohlendorf et al.

[11] Patent Number: 5,312,553
[45] Date of Patent: May 17, 1994

[54] MIXTURES OF ORGANIC AMMONIUM SALTS AS FLOW ACCELERATORS

[75] Inventors: Dieter Ohlendorf, Liederbach; Manfred Hofinger, Burgkirchen; Detlef Wehle, Kastl/Obb., all of Fed. Rep. of Germany

[73] Assignee: Hoechst Aktiengesellschaft, Frankfurt am Main, Fed. Rep. of Germany

[21] Appl. No.: 391,176

[22] Filed: Aug. 9, 1989

[30] Foreign Application Priority Data

Aug. 11, 1988 [DE] Fed. Rep. of Germany ....... 3827183

[51] Int. Cl.$^5$ .......................... C09K 3/00; B01F 17/18
[52] U.S. Cl. .......................... 252/1; 252/76; 252/77; 252/78.1; 252/355; 252/356; 252/357; 252/DIG. 7
[58] Field of Search ............ 252/182.23, 355, 356, 252/357, 76, 77, 78.1, DIG. 7

[56] References Cited

U.S. PATENT DOCUMENTS

| | | | |
|---|---|---|---|
| 4,615,825 | 10/1986 | Teot et al. | 252/356 |
| 4,705,860 | 11/1987 | Ohlendorf et al. | 546/347 |
| 4,735,731 | 4/1988 | Rose et al. | 252/8.51 |
| 4,828,765 | 5/1989 | Ohlendorf et al. | 564/285 |
| 4,881,566 | 11/1989 | Ubels et al. | 137/13 |

FOREIGN PATENT DOCUMENTS

83-01583  5/1983  PCT Int'l Appl. .

*Primary Examiner*—Edward A. Miller

[57] ABSTRACT

Mixtures of organic ammonium salts composed of 20 to 80% of a quaternary ammonium salt of the formula

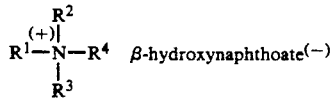

and 80 to 20% by weight of an amine salt of the formula

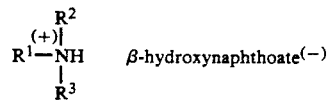

where in both formulae $R^1$ denotes $C_{12}$–$C_{26}$-alkyl, $C_{12}$–$C_{26}$-alkenyl, $C_{12}$–$C_{26}$-fluoroalkyl, $C_{12}$–$C_{26}$-fluoroalkenyl or a group of the formula

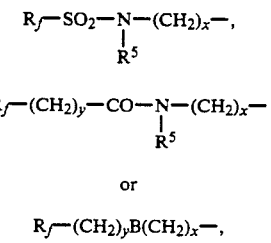

$R^2$ and $R^3$ denote $C_1$–$C_3$-alkyl, preferably methyl,
$R^4$ denotes $C_1$–$C_4$-alkyl and, for the case where $R^1$=alkyl or alkenyl, also a group of the formula $-(C_2H_4O)_zH$,
$R_f$ denotes $C_8$–$C_{20}$-fluoroalkyl or $C_8$–$C_{20}$-fluoroalkenyl,
$R^5$ denotes hydrogen, methyl or ethyl,
B denotes oxygen or sulfur,
x denotes an integer from 2 to 6,
y denotes 0, 1 or 2, and
z denotes numbers from 1 to 4, and additionally 30–70 mole %, preferably 40–60 mole %, particularly preferably 50 mol %, of alkali-metal salicylate calculated on the basis of the total amount of $\beta$-hydroxynaphthoic acid.

11 Claims, 2 Drawing Sheets

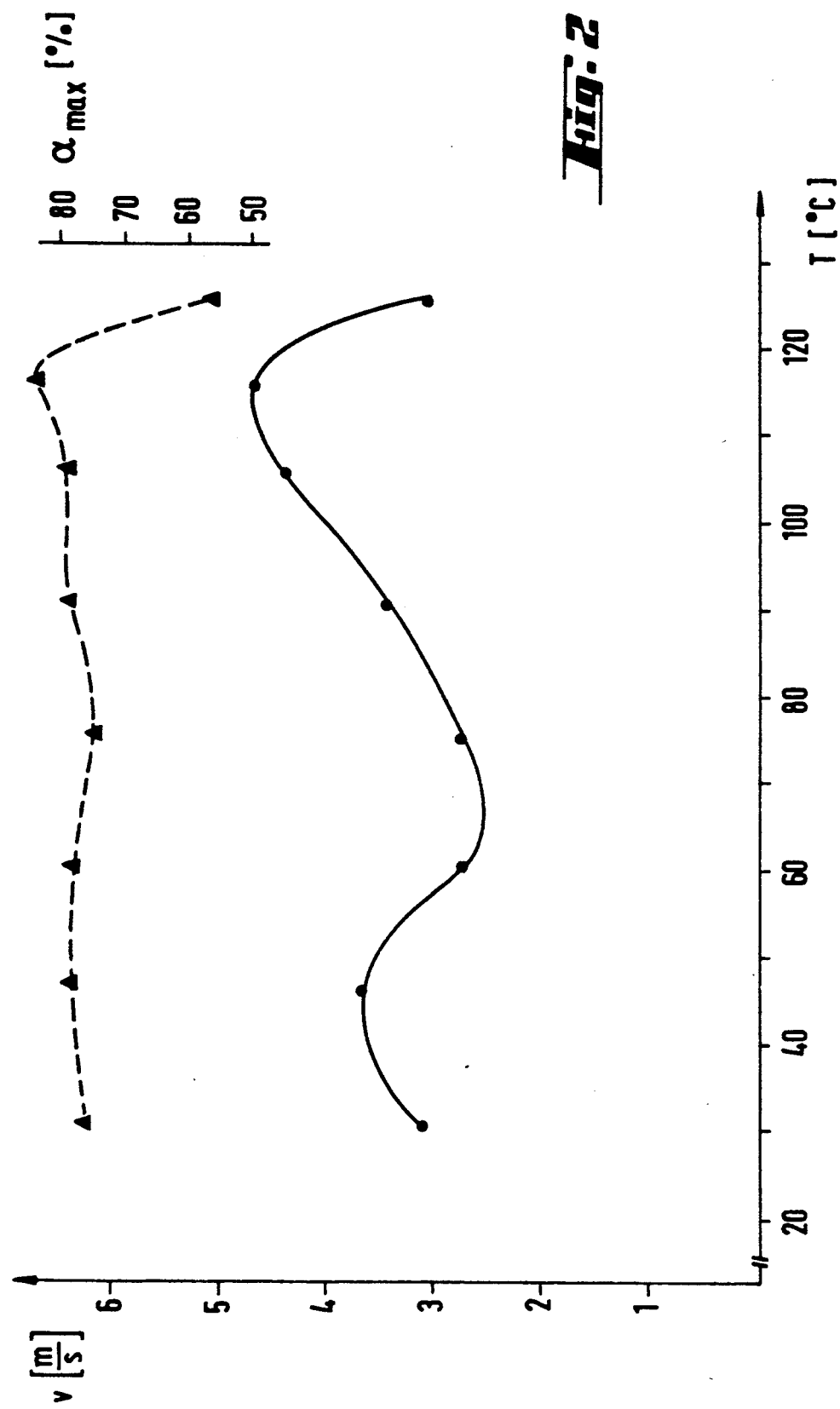

MIXTURES OF ORGANIC AMMONIUM SALTS AS FLOW ACCELERATORS

It is already known that quaternary ammonium salts which contain a long-chain alkyl group may be used as flow accelerators (DE-A 3,212,969, U.S. Pat. No. 4,705,860, U.S. Pat. No. 4,828,765, DE-A 3,347,378, WO 83/61,583). This literature also describes how the action as flow accelerator can be intensified if other electrolytes such as, for instance, simple inorganic salts ($NaCl$, $CuCl_2$, $Na_2CO_3$) or salts of organic acids such as Na benzoate or Na salicylate are additionally added to the quaternary ammonium salts. Preferably, in such cases, a salt which contains the same anion as the quaternary ammonium compound itself is taken as additional electrolyte. Although an intensification of the action as flow accelerator is achieved with such mixtures, precisely as also the quaternary ammonium salts themselves, these mixtures develop their action generally only in a relatively narrow temperature interval.

It has now been found than an action as flow accelerator can be achieved over a very much wider temperature range compared to the mixtures hitherto described with the mixtures of salts described below which contain both β-hydroxynaphthoate and also salicylate.

The invention consequently relates to mixtures of organic ammonium salts composed of a quaternary ammonium salt of the formula 1

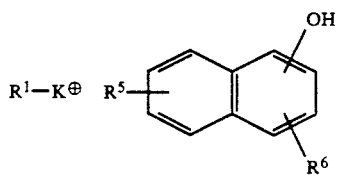 (1)

wherein

K denotes a group of the formula

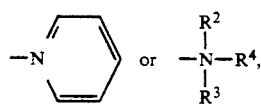

$R^1$ denotes $C_{12}$–$C_{26}$-alkyl, $C_{12}$–$C_{26}$-alkenyl, $C_{12}$–$C_{26}$-fluoroalkyl, $C_{12}$–$C_{26}$-fluoroalkenyl or a group of the formulae

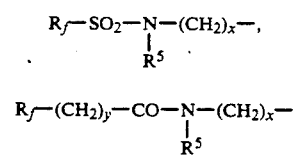

$R^2$ and $R^3$ denote $C_1$–$C_3$-alkyl, preferably methyl,
$R^4$ denotes $C_1$–$C_4$-alkyl and, for the case where $R^1$=alkyl or alkenyl, also a group of the formula $-(C_2H_4O)_2H$,
$R_f$ denotes $C_8$–$C_{20}$-fluoroalkyl or $C_8$–$C_{20}$-fluoroalkenyl,
$R^5$ denotes hydrogen, methyl or ethyl,
$R^6$ denotes $-COO^\ominus$ or $-SO^\ominus_3$,
$R^7$ denotes hydrogen or methyl,
B denotes oxygen or sulfur,
x denotes an integer from 2 to 6,
y denotes 0, 1 or 2, and
z denotes numbers from 1 to 4,
it being possible, in the case where K denotes a group of the formula

and $R^4$ denotes a group of the formula $-(C_2H_4O)_2H$, for said quaternary ammonium salts also to be replaced in an amount of 20 to 80% by weight by the corresponding amine salts of the formula

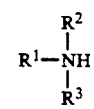

and additionally an alkali-metal salt of an anion of the formula 2

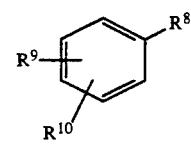 (2)

wherein
$R^8$ denotes $-COO^\ominus$ or $-SO^{63}{}_3$, $R^9$ denotes hydrogen, hydroxyl, $NO_2$, fluorine, chlorine, bromine or iodine and $R^{10}$ denotes $C_1$–$C_5$-alkyl, $C_2$–$C_5$-alkenyl or $C_1$–$C_5$-alkoxy, in an amount of 30 to 70, preferably 40 to 60, particularly preferably 50, mol %, based on the total amount present of anion in the compound of formula 1.

The quaternary ammonium and amine salts contain, according to the above formula, equivalent amounts of cations and anions. It is also possible, however, that one of the two ions is present in excess. The missing amount of the corresponding counterions is then compensated for by counterions of the other type, for example Na or Cl ions.

Preferred are those mixtures in which K denotes a group of the formula

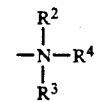

and A denotes β-hydroxynaphthoate.

Particularly preferred are those mixtures which contain quaternary ammonium salts of the formula

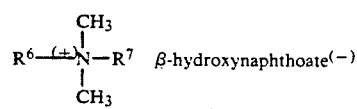

and amine salts of the formula

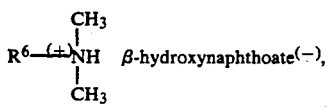

where $R^6$ denotes $C_{14}$-$C_{22}$-alkyl, $R^7$ denotes methyl or the group —$(C_2H_4O)_zH$ and z denotes numbers from 1 to 4. These mixtures preferably contain 20 to 80% by weight of the quaternary ammonium salt and correspondingly 80 to 20% by weight of the amine salt. In the case of the anions of the formula 2, the salicylate anion is preferred.

BRIEF DESCRIPTION OF THE DRAWING

In the accompanying Drawing,

FIG. 2 is a graphical plot of the corresponding values when Na salicylate is added to the same flow accelerator.

Figure 1:
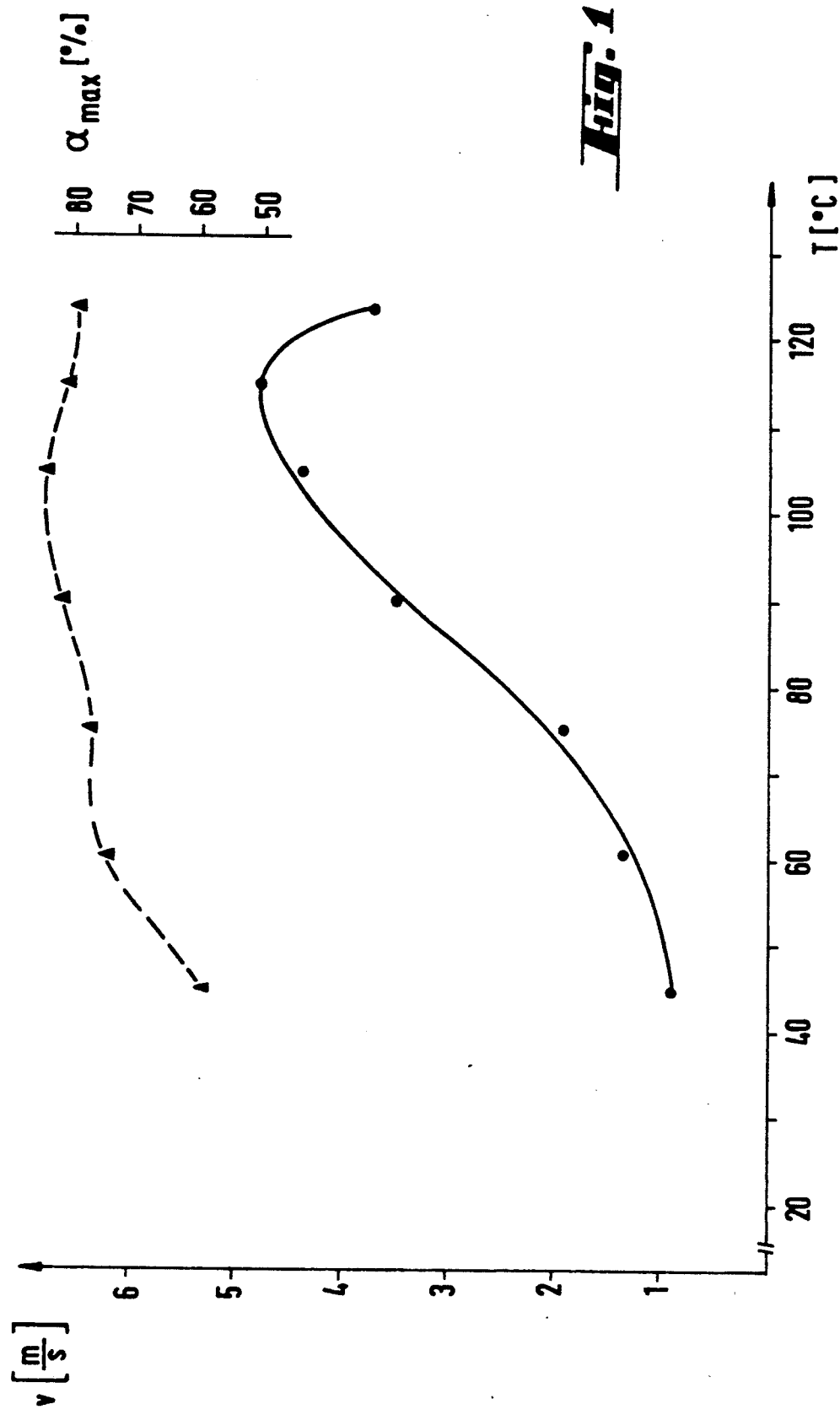
FIG. 1 is a graphical plot of values obtained for a flow accelerator which does not include a salicylate.

The mixtures of quaternary ammonium salts and amine salts are prepared by known methods by alkylation of the basic tertiary amines, for example with alkyl halides or dialkyl sulfate. The quaternary ammonium salts in which $R^4$ represents a polyoxyethylene radical are prepared by oxalkylating quaternization of the tertiary amines by known methods (EP-A 379,260, U.S. Pat. No. 2,836,517, U.S. Pat. No. 1,223,730, U.S. Pat. No. 3,223,718, U.S. Pat. No. 2,897,170).

In the salts thus obtained, which contain a halide or methosulfate ion, said ions are exchanged by ion exchange by known methods for the ion of the formula

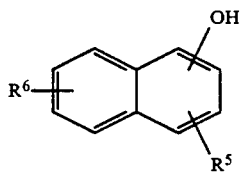

for example, by reacting β-hydroxynaphthoic acid with the hydroxide of the quaternary ammonium compound. Said hydroxide may be obtained in turn from the corresponding ammonium halide using silver hydroxide. Preferably, the naphthoate salt is prepared by double reaction of tetraalkylammonium halides with alkali-metal hydroxide and napthoic acid in a 2-phase system composed of water and a solvent which is not miscible with water, as described in DE-A 3,516,843.

An alkali-metal salt of an anion of the formula

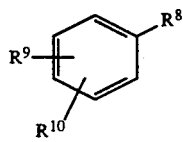

preferably sodium salicylate, is added to these mixtures of ammonium salts and possible corresponding amine salts or their aqueous solutions in amounts of 50 mol %, based on the total amount of the ion of the formula

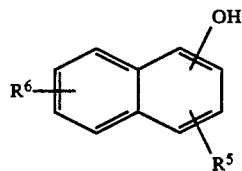

calculated as free acid. The alkali-metal salt of the anion of the formula (2) may be added in solid form or as an aqueous solution to the solution of the salts of the formula 1. In total, the aqueous solutions should contain preferably 30 to 40% by weight of solid. For the application as flow accelerator in turbulently flowing aqueous media, for example in cooling and heating circuits, said solutions are further diluted to a solid concentration of 0.01 to 5, preferably 0.05 to 1% by weight.

As described above an action as flow accelerator is obtained over a very wide temperature range with salts which contain β-hydroxynaphthoate and salicylate. This principle is generally valid also for other combinations of quaternary ammonium salts, such as have been described in the prior art cited in the introduction, with other salts. In that case, the particular anions should be so selected that the combination of one anion with the quaternary ammonium cation is effective as a flow accelerator in a relatively low temperature range and the combination of the other anion with the same quaternary cation is effective in a relatively high temperature range.

Such mixtures are effective in a greater temperature range as flow accelerators than the individual components and, in particular, over the entire temperature range of the two individual components taken together. Furthermore, the effectiveness of the reduction in friction, i.e. maximum achievable flow velocity, before the reduction in friction collapses is considerably improved in the lower half of the temperature range.

Preparation of Octadecyldimethylhydroxyethylammonium β-Hydroxynaphthoate (EO-OBON)

181.6 g (0.60 mol; alkali number: 185.4 mg KOH/g) of octadecyldimethylamine (tert. N 99.4 eq-%), 114.6 g (0.60 mol; acid number: 293.3 mg KOH/g) of β-hydroxynaphthoic acid, 194.4 g (10.8 mol) of demineralized water and 60.4 g (10% m/m) of isopropanol are placed in a 1 l laboratory glass autoclave. After flushing twice with nitrogen, the reaction mixture is heated to 75° C. After letting down the pressure built up in this process, 59.2 ml (1.20 mol) of ethylene oxide are added while stirring (approx. 500 rev/min) continuously in the course of 2 hours via a pressure lock in a manner such that the internal temperature does not rise above 80° C. While the ethylene oxide is being added, the internal pressure rises to a maximum of 1.6 bar.

After a reaction time of a further 8 hours, the pressure is let down and the product is incipiently distilled in a vacuum rotary evaporator (bath temperature 70° C.). A total of 39 g is distilled off and 591 g of a brownish yellow solution (formation of a precipitate when allowed to stand for a prolonged period at room temperature) is thus obtained which contains 59% solids, 5.5% isopropanol, 4.3% ethylene glycol, 0.2% diethylene glycol and 30% water. The content of ethylene oxide is 1.3 ppm. The degree of quaternization determined by an Epton's titration (titration at pH 1-2 and pH ≧10) is 47.4%.

To prepare the mixture of EO-OBON with sodium salicylate, 48 g (0.30 mol, 50 mol % based on the β-hydroxynaphthoic acid used) of sodium salicylate is added to the product (591 g) obtained after the incipient distillation at a temperature of 50° C. and stirring is carried out for 1 hour at said temperature.

Measuring Apparatus

To measure the reduction in friction, use is made of a closed flow apparatus in which the test solution is circulated by pumping. The measuring distance for determining the pressure loss ΔP is 1 m, the tube diameter is 6 mm and the ratio of the inlet length 1 to the tube diameter d (1/d) is 280. The flow velocity V is determined using an inductive flow meter. The entire test apparatus (entire volume of solution) can be temperature-controlled to ±3° C. from 10° C. to 150° C.

Before the measurements were carried out, the solutions were in each case pumped through the apparatus at least for 2 hours at the measuring temperature. Before the measurements were carried out at temperatures of less than or equal to 45° C., the solutions were temperature-controlled at the respective temperatures by recirculation overnight or, if possible, over the weekend.

After pouring the solutions into the measuring apparatus, the solutions were heated to at least 120° C. generally while recirculating and only then cooled to the respective measuring temperature again.

The solutions mentioned were investigated for their effectiveness as flow accelerators in the normal manner by measuring, for various flow velocities V, the pressure drop ΔP for the particular aqueous solution of the surfactants over the distance l while flowing through a tube having the cross section d.

From these values the dimensionless quantities of coefficient of friction λ and the Reynolds number Re can be calculated:

$$\lambda = \frac{2d}{\rho V^2} \cdot \frac{\Delta P}{L}$$

$$Re = \frac{V \cdot d}{\nu}$$

where $\rho$ denotes the density and $\nu$ denotes the kinematic viscosity. Normally, the corresponding values of the pure solvent, water, are used in each case for $\rho$ and $\nu$. The values of λ and Re thus obtained for the surfactant solutions investigated were compared, in the normal double-logarithmic plot of λ against Re, with the corresponding values for pure water, which are given by $$1/\sqrt{\lambda} = 2\log Re \sqrt{\lambda} - 0.8$$

A FA action or, alternatively, reduction in friction exists if it is the case that:

$\lambda_{H_2O} - \lambda_{FA} > 0$ or the magnitude of the reduction in friction in percentage is calculated according to:

$$\alpha = \% \text{ reduction in friction} = \frac{\lambda_{H_2O} - \lambda_{FA}}{\lambda_{H_2O}} \times 100$$

The degree of effectiveness of a surfactant solution as FA will be characterized below by the magnitude of $Re_{max}$; accordingly, a surfactant solution having $Re_{max} = 20,000$ has a better effectiveness as FA than a surfactant solution having $Re_{max} = 10,000$. The associated α-value will be characterized by $\alpha_{max}$.

The tables in the following examples show the measured values for the flow velocity V, for $Re_{max}$ and $\alpha_{max}$ at various temperatures.

EXAMPLE 1

TABLE 1

Octadecyldimethylhydroxyethylammonium 3-hydroxy-2-naphthoate, concentration: 1,000 ppm

| T/°C. | $V_{max}$ (m/s) | $Re_{max} \times 10^{-3}$ | $\alpha_{max}$ (% reduction in friction) |
|---|---|---|---|
| 45 | 0.92 | 9,300 ± 950 | 60 ± 3 |
| 60 | 1.36 | 17,000 ± 1,700 | 75 ± 4 |
| 75 | 1.93 | 29,500 ± 3,000 | 77 ± 4 |
| 90 | 3.51 | 64,800 ± 6,500 | 82 ± 4 |
| 105 | 4.39 | 94,100 ± 9,500 | 84 ± 4 |
| 115 | 4.77 | 110,400 ± 11,000 | 81 ± 4 |
| 123 | 3.69 | 90,900 ± 9,100 | 80 ± 4 |

TABLE 2

Octadecyldimethylhydroxymethylammonium 3-hydroxy-2-naphthoate, concentration 1,000 ppm + 2 mmole/l sodium salicylate

| T/°C. | $V_{max}$ (m/s) | $Re_{max} \times 10^{-3}$ | $\alpha_{max}$ (% reduction in friction) |
|---|---|---|---|
| 30 | 3.13 | 23,600 ± 2,500 | 75 ± 4 |
| 46 | 3.68 | 36,900 ± 3,700 | 78 ± 4 |
| 60 | 2.77 | 34,600 ± 3,500 | 77 ± 4 |
| 75 | 2.78 | 42,400 ± 4,500 | 74 ± 4 |
| 90 | 3.45 | 63,800 ± 6,500 | 79 ± 4 |
| 105 | 4.40 | 94,100 ± 9,500 | 79 ± 4 |
| 115 | 4.69 | 108,800 ± 11,000 | 84 ± 4 |
| 125 | 3.09 | 76,800 ± 8,000 | 56 ± 3 |

Table 1 shows the values for a quaternary ammonium β-hydroxynaphthoate without salicylate added, while Table 2 gives the corresponding values for the same compound but with Na salicylate added. These values are shown graphically in FIGS. 1 and 2.

The comparison of the lower curves of the two figures, which represent the flow velocity, shows that the magnitude of the reduction in friction (flow velocity) is maintained at high temperatures by adding salicylate and, in addition, is also extended to the low-temperature region. This finding was surprising since, in both cases, the concentration of the quaternary ammonium cation remains the same, and the effect of the increase in the reduction in friction (flow velocity) at low temperatures must therefore be attributed to the mixture of various cations. However, on its own, on the other hand, Na salicylate has no action as a flow accelerator taken on its own.

TABLE 3

Octadecyldimethylhydroxyethylammonium 3-hydroxy-2-naphthoate, concentration 1,000 ppm + 0.5 mmole/l sodium salicylate

| T/°C. | $V_{max}$ (m/s) | $Re_{max} \times 10^{-3}$ | $\alpha_{max}$ (% reduction in friction) |
|---|---|---|---|
| 20 | 1.32 | 7,940 | 57.6 |
| 30 | 1.59 | 11,900 | 63.0 |
| 50 | 2.36 | 25,300 | 72.0 |
| 70 | 2.36 | 34,000 | 74.5 |
| 90 | 2.99 | 54,700 | 78.26 |
| 110 | 4.7 | 105,000 | 78.82 |
| 120 | 4.77 | 115,000 | 68.91 |

TABLE 3-continued

Octadecyldimethylhydroxyethylammonium
3-hydroxy-2-naphthoate, concentration 1,000 ppm +
0.5 mmole/l sodium salicylate

| T/°C. | $V_{max}$ (m/s) | $Re_{max} \times 10^{-3}$ | $\alpha_{max}$ (% reduction in friction) |
| --- | --- | --- | --- |
| 125 | 3.89 | 97,000 | 56.94 |

TABLE 4

Octadecyldimethylhydroxyethylammonium
3-hydroxy-2-naphthoate, concentration 1,000 ppm +
2 mmole/l sodium salicylate

| T/°C. | $V_{max}$ (m/s) | $Re_{max} \times 10^{-3}$ | $\alpha_{max}$ (% reduction in friction) |
| --- | --- | --- | --- |
| 21  | 6.83 | 42,000  | 78.53 |
| 30  | 6.44 | 48,500  | 78.28 |
| 50  | 5.55 | 59,800  | 78.87 |
| 70  | 4.62 | 42,300  | 78.49 |
| 90  | 3.0  | 55,000  | 76.68 |
| 110 | 4.57 | 103,000 | 74.98 |
| 120 | 3.28 | 79,300  | 59.90 |

Tables 3 and 4 show how various concentrations of Na salicylate influence the effect described. From the tables it emerges that, although an unduly high concentration of Na salicylate considerably improves the magnitude of the reduction in friction at low temperatures, it impairs it at high temperatures. For the practical application, however, a reduction in friction as constant as possible over the entire temperature range is desirable.

In the following Examples 2 to 4, it is shown for other quaternary ammonium salts that the addition of Na salicylate expands the range in which a reduction in friction occurs to low temperatures.

EXAMPLE 2

TABLE 5

Octadecyltrimethylammonium 3-hydroxy-2-
naphthoate, concentration: 500 ppm

| T/°C. | $V_{max}$ (m/s) | $Re_{max} \times 10^{-3}$ | $\alpha_{max}$ (% reduction in friction) |
| --- | --- | --- | --- |
| 61  | 0.86 | 10,900 | 71.02 |
| 70  | 1.24 | 17,800 | 74.43 |
| 80  | 2.29 | 50,200 | 77.53 |
| 100 | 2.73 | 55,100 | 79.23 |
| 110 | 3.39 | 75,300 | 80.31 |
| 120 | 3.37 | 81,000 | 81.54 |
| 127 | 1.35 | 34,100 | 68.98 |

TABLE 6

Octadecyltrimethylammonium 3-hydroxy-2-
naphthoate, concentration: 500 ppm + $10^{-3}$ mole/l
sodium salicylate

| T/°C. | $V_{max}$ (m/s) | $Re_{max} \times 10^{-3}$ | $\alpha_{max}$ (% reduction in friction) |
| --- | --- | --- | --- |
| 44  | 0.45 | 4,340  | 47.01 |
| 50  | 1.03 | 11,000 | 66.58 |
| 60  | 2.47 | 30,900 | 73.77 |
| 70  | 2.36 | 33,900 | 75.80 |
| 80  | 3.18 | 51,900 | 76.31 |
| 100 | 3.52 | 71,700 | 81.86 |
| 110 | 3.40 | 70,000 | 82.93 |
| 120 | 2.64 | 63,700 | 74.07 |
| 125 | 1.56 | 38,900 | 18.58 |

EXAMPLE 3

TABLE 7

Hexadecyltrimethylammonium 3-hydroxy-2-
naphthoate, concentration: 500 ppm

| T/°C. | $V_{max}$ (m/s) | $Re_{max} \times 10^{-3}$ | $\alpha_{max}$ (% reduction in friction) |
| --- | --- | --- | --- |
| 40  | 1.02 | 9,300  | 58.88 |
| 60  | 2.28 | 28,300 | 72.63 |
| 80  | 3.35 | 54,300 | 77.79 |
| 90  | 3.29 | 60,300 | 77.00 |
| 100 | 2.58 | 52,800 | 77.72 |
| 104 | 1.85 | 39,400 | 76.99 |
| 107 | 1.78 | 39,000 | 54.71 |

TABLE 8

Hexadecyltrimethylammonium 3-hydroxy-2-
naphthoate, concentration: 500 ppm + $10^{-3}$ mole/l
sodium salicylate

| T/°C. | $V_{max}$ (m/s) | $Re_{max} \times 10^{-3}$ | $\alpha_{max}$ (% reduction in friction) |
| --- | --- | --- | --- |
| 25  | 0.78 | 5,270  | 58.11 |
| 40  | 1.56 | 14,300 | 68.78 |
| 60  | 2.80 | 34,900 | 75.81 |
| 80  | 3.25 | 52,900 | 77.78 |
| 90  | 3.26 | 59,900 | 78.22 |
| 100 | 2.49 | 51,000 | 77.63 |
| 105 | 1.83 | 39,100 | 44.32 |

EXAMPLE 4

TABLE 9

Docosyltrimethylammonium 3-hydroxy-2-
naphthoate, concentration: 1,000 ppm

| T/°C. | $V_{max}$ (m/s) | $Re_{max} \times 10^{-3}$ | $\alpha_{max}$ (% reduction in friction) |
| --- | --- | --- | --- |
| 80  | 1.0 | 16,500 | 60 |
| 90  | 4.5 | 83,000 | 75 |
| 100 | 4.0 | 81,700 | 77 |
| 110 | 3.3 | 74,000 | 78 |
| 120 | 3.0 | 73,200 | 78 |
| 130 | 2.7 | 71,200 | 80 |
| 140 | 2.5 | 70,700 | 82 |
| 145 | 2.5 | 73,100 | 81 |
| 150 | 1.5 | 45,300 | 65 |

TABLE 10

Docosyltrimethylammonium 3-hydroxy-2-naphthoate,
concentration: 1,000 ppm + 1.8 mmole/l sodium salicylate

| T/°C. | $V_{max}$ (m/s) | $Re_{max} \times 10^{-3}$ | $\alpha_{max}$ (% reduction in friction) |
| --- | --- | --- | --- |
| 50  | 2.21 | 23,600 | 73.01 |
| 60  | 2.38 | 29,700 | 76.57 |
| 70  | 3.06 | 43,700 | 76.99 |
| 80  | 4.14 | 67,600 | 77.17 |
| 95  | 3.59 | 69,600 | 77.57 |
| 110 | 3.0  | 67,100 | 78.2  |
| 125 | 2.69 | 67,300 | 77.63 |
| 130 | 3.0  | 77,500 | 73.65 |
| 135 | 2.69 | 71,600 | 82.7  |
| 140 | 2.67 | 73,500 | 81.8  |
| 145 | 2.0  | 56,900 | 82.65 |

We claim:

1. A salt mixture comprising: a quaternary ammonium salt of the formula (1)

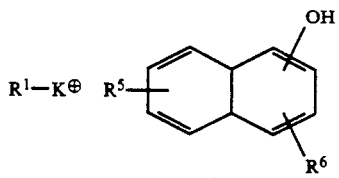
(1)

the above right-hand structure being the anion, wherein

R denotes a group of the formula

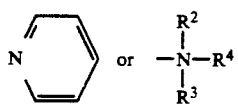

$R^1$ denotes $C_{12}$-$C_{26}$alkyl, $C_{12}$-$C_{26}$alkenyl, $C_{12}$-$C_{26}$-fluoroalkyl, $C_{12}$-$C_{26}$-fluoralkenyl or a group of the formulae

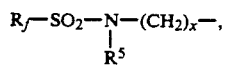

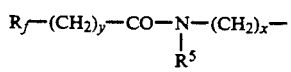

or

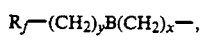

$R^2$ and $R^3$ denote $C_1$-$C_3$-alkyl,
$R^4$ denotes $C_1$-$C_3$-alkyl and, for the case where $R^1$=alkyl or alkenyl, also a group of the formula $-(C_2H_4O)_zH$,
$R_f$ denotes $C_8$-$C_{20}$fluoroalkyl or $C_8$-$C_{20}$-fluoroalkenyl,
$R^5$ denotes hydrogen, methyl or ethyl,
$R^6$ denotes $-COO\ominus$ or $-SO_3\ominus$,
$R^7$ denotes hydrogen or methyl,
B denotes oxygen or sulfur,
x denotes an integer from 2 to 6,
y denotes 0, 1 or 2, and
z denotes numbers from 1 to 4,
and an alkali metal salt of an anion of the formula 2

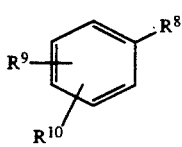
(2)

wherein $R^8$ denotes $-COO\ominus$ or $-SO_3\ominus$, $R^9$ denotes hydrogen, hydroxyl, $CO_2$, fluorine, chlorine, bromine or iodine and $R^{10}$ denotes $C_1$-$C_5$-alkyl, $C_2$-$C_5$-alkenyl or $C_1$-$C_5$alkoxy, in a quantity of 30 to 70 mol %, based on the total amount of said anion.

2. A salt mixture as claimed in claim 1 containing a compound of the formula 1, wherein K denotes a group of the formula

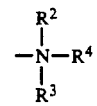

and the anion of formula 2 is β-hydroxynaphthoate.

3. A salt mixture as claimed in claim 1, wherein the anion of the formula 2 is salicylate.

4. A salt mixture as claimed in claim 1 containing a compound of the formula (1), wherein, said formula (1), K denotes a group of the formula

$R^4$ being a group of the formula $-(C_2H_4O)_zH$, said salt mixture optionally further comprising an amine salt having the cation

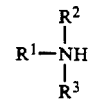

the anion of said amine salt being said anion of formula (I); the resulting mixture of cations, when said amine salt is optionally included, comprising 20 to 80%

and 80 to 20% $R^1$-$K\oplus$.

5. A salt mixture as claimed in claim 4, wherein the said quaternary ammonium salt is

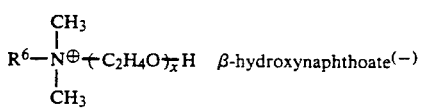

and the amine salt is

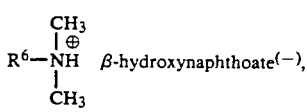

where $R^6$ denotes $C_{14}$-$C_{22}$-alkyl, and x denotes a number from 1 to 4.

6. A salt mixture as claimed in claim 1, wherein said quaternary ammonium salt is a β-hydroxynaphthoate having a cation of the formula

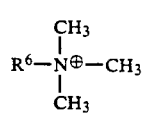

said salt mixture further comprising a β-hydroxynaphthoate amine salt having the cation

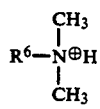

wherein $R^6$ denotes $C_{14}$–$C_{22}$ alkyl.

7. A salt mixture as claimed in claim 1, further comprising water, the amount of the salt mixture being 0.01 to 5% by weight of the solution formed.

8. The salt mixture as claimed in claim 1, wherein $R^2$ denotes a methyl.

9. The salt mixture as claimed in claim 1, wherein $R^2$ and $R^3$ denote methyl.

10. The salt mixture as claimed in claim 1, wherein $R^{10}$ denotes $C_1$–$C_5$-alkyl, $C_2$–$C_5$-alkenyl or $C_1C_5$-alkoxy in quantity of 40 to 60 mol % based on the total amount of said anion.

11. The salt mixture as claimed in claim 1, wherein $R^{10}$ denotes $C_1$–$C_5$-alkyl, $C_2$–$C_5$-alkenyl or $C_1$–$C_5$-alkoxy in a quantity of 50 mol % based on the total amount of said anion.

* * * * *